US006832615B2

(12) United States Patent
Hensel (10) Patent No.: US 6,832,615 B2
(45) Date of Patent: Dec. 21, 2004

(54) SURFACE MOUNTABLE FLOSS CONTAINER (76) Inventor: Keith James Hensel, 15 Bongalong Street, Naremburn, New South Wales 2065 (AU)

( * ) Notice: Subject to any disclaimer, the term of this patent is extended or adjusted under 35 U.S.C. 154(b) by 99 days.

(21) Appl. No.: 10/181,024
(22) PCT Filed: Jan. 12, 2001
(86) PCT No.: PCT/AU01/00021
§ 371 (c)(1),
(2), (4) Date: Nov. 4, 2002
(87) PCT Pub. No.: WO01/50980
PCT Pub. Date: Jul. 19, 2001

(65) Prior Publication Data
US 2003/0116449 A1 Jun. 26, 2003

(30) Foreign Application Priority Data
Jan. 12, 2000 (AU) .............................................. PQ5053

(51) Int. Cl.[7] .............................................. A61B 19/02
(52) U.S. Cl. ........................ 132/321; 206/63.5; 206/829
(58) Field of Search ................................. 132/321, 324, 132/325; 220/483; D28/66; 206/63.5, 829; 248/146

(56) References Cited

U.S. PATENT DOCUMENTS

| 1,455,673 | A | | 5/1923 | Shalek | |
|---|---|---|---|---|---|
| 1,899,242 | A | | 2/1933 | McNab | |
| 1,984,610 | A | | 2/1934 | Warren | ......................... 221/60 |
| 2,177,504 | A | | 10/1939 | Thompson | ............... 312/112.5 |
| D154,894 | S | | 8/1949 | Bashore | ......................... D24/1 |
| 2,542,400 | A | * | 2/1951 | Donofrio | ..................... 248/362 |
| 2,725,270 | A | | 11/1955 | Upchurch | ................... 312/207 |
| 3,476,261 | A | * | 11/1969 | McCutcheon et al. | ......... 211/74 |
| 3,489,324 | A | | 1/1970 | Stohl | ............................ 225/37 |
| 3,892,369 | A | * | 7/1975 | Fujawa | ..................... 242/597.4 |
| 4,001,444 | A | * | 1/1977 | Clarke | ......................... 426/110 |
| 4,012,007 | A | | 3/1977 | Cunningham | ............ 242/55.54 |
| 4,020,975 | A | * | 5/1977 | Stauffer | ......................... 222/93 |
| 4,934,640 | A | | 6/1990 | Bichon | ..................... 248/206.2 |
| 4,938,346 | A | * | 7/1990 | Urbano | ...................... 206/77.1 |
| 5,087,005 | A | | 2/1992 | Holoff et al. | ............. 248/205.8 |
| 5,163,561 | A | | 11/1992 | Fitzgerald | .................... 206/581 |
| 5,163,566 | A | * | 11/1992 | Hempel | ........................ 211/65 |
| 5,215,193 | A | | 6/1993 | Dennis | ........................ 206/223 |
| 5,299,723 | A | * | 4/1994 | Hempel | ........................ 225/38 |
| 5,332,107 | A | | 7/1994 | Williams | ....................... 211/88 |
| 5,680,933 | A | * | 10/1997 | Miller | ......................... 206/581 |
| 5,742,971 | A | | 4/1998 | Salinger | ..................... 15/167.1 |
| 5,954,257 | A | | 9/1999 | Panneri | ........................ 225/39 |
| 6,000,575 | A | * | 12/1999 | LaCour et al. | .............. 220/739 |
| D454,226 | S | | 3/2002 | Scarpelli | ....................... D28/66 |
| D456,565 | S | | 4/2002 | Scarpelli | ....................... D28/66 |
| D460,838 | S | | 7/2002 | Scarpelli | ....................... D28/66 |

FOREIGN PATENT DOCUMENTS

| AT | 216410 | 7/1961 |
|---|---|---|
| FR | 1044878 | 11/1953 |

* cited by examiner

Primary Examiner—Todd E. Manahan
(74) Attorney, Agent, or Firm—Levy & Grandinetti

(57) ABSTRACT

A container (10) to receive products such as an air freshener, disinfectant or deodoriser, or alternatively tape twine or dental floss. The container (10) has a hollow body (13) attached to a suction cup (25) by means of a hollow stem of the body (11) and a projection (26) of cup (25). When the cup (25) is attached to a supporting surface the skirt (18) of the body (13) terminates adjacent the supporting surface and/or cup (25) to inhibit tilting of the body (13). The body (13) cooperates with a wall (29) of the cup (25) to enclose a space within which the product is located.

19 Claims, 7 Drawing Sheets

SURFACE MOUNTABLE FLOSS CONTAINER

This application is the U.S. National Phase of PCT Application Number PCT/AU01/00021, filed on Jan. 12, 2001, which claims priority to Australian Provisional Application Number PQ5053, filed Jan. 12, 2000.

TECHNICAL FIELD

The present invention relates to containers and more particularly but not exclusively to containers which are mountable on a smooth surface to dispense thread or ribbon type products, such as dental floss and adhesive tape, as well as containers to receive air freshener and deodoriser material.

BACKGROUND OF THE INVENTION

Frequently, use of items such as dental floss and adhesive tape is inhibited by the product not being readily accessible. Still further, frequently, time is lost in trying to locate commonly used items such as dental floss and adhesive tape as they tend to be moved from the location of their intended use or a location at which they are intended to be stored. A still further disadvantage of containers which dispense thread or tape type products is that frequently both hands are required to remove the product from within the container.

Air fresheners are often required in areas that are tiled, such as bathrooms, laundries and kitchens. Although air fresheners and deodorisers are available, they are generally not suitable for positioning on vertical surfaces, such as tiled surfaces.

OBJECT OF THE INVENTION

It is the object of the present invention to overcome or substantially ameliorate at least one of the above disadvantages.

SUMMARY OF THE INVENTION

There is disclosed herein a container to receive a product, said container having:
- a hollow body within which the product is to be supported, said body having at least one peripheral skirt generally surrounding a transverse wall;
- a suction cup having a central portion attached to the transverse wall, and a cup flange extending from the central portion generally towards the peripheral skirt; and wherein
- said suction cup is secured to a supporting surface by applying a force to said transverse wall, towards said suction cup to resiliently deform the suction, cup against said supporting surface, so that said peripheral skirt terminates adjacent or is abutting said cup flange or supporting surface when said suction cup is secured to said supporting surface to inhibit tilting of said hollow body relative to said suction cup and a disengagement of said suction cup from said supporting surface.

Preferably, said transverse wall is an end wall and said product is to be located between said transverse wall and cup flange.

Preferably, said hollow body is relatively stiff with respect to said suction cup.

Preferably, said peripheral skirt has a recess facing said cup flange, and said cup flange has a cup wall movably received within said recess.

Preferably said recess is a space between a first skirt flange and a second skirt flange of said peripheral skirt.

Preferably, said suction cup is provided with a tab projecting outward of the said peripheral skirt which is gripped to deform the suction cup to release the suction cup from said supporting surface.

Preferably, there is extending from said end wall, a hollow stem to which said suction cup is attached by a projection extending into said stem.

Preferably said peripheral skirt and said cup skirt each have one of a projection or opening wherein said projections will enter said opening to prevent relative rotation of said hollow body and said suction cup.

Preferably the product is a dental floss.

There is further disclosed herein a container to receive a product, said container having: a hollowed body within which the product is to be supported, said body having a peripheral skirt generally surrounding a transverse wall, said peripheral skirt having an extremity and a recess extending from the extremity inwardly of the peripheral skirt; and
- a suction cup having a central portion attached to the transverse wall, and a cup flange extending from the central portion generally towards the peripheral skirt, said suction cup further having a suction cup wall extending from the cup flange and into said recess; and wherein
- said suction cup is secured to a supporting surface by applying a force to the body towards said suction cup to resiliently deform the suction cup against said supporting surface and to further cause movement of the suction cup wall into said recess.

Preferably the suction cup wall includes spaced wall portions adjacent said cup flange, the wall portions being spaced by a recess surrounding said cup flange.

Preferably the wall portions include an inner and an outer wall portion, with said outer wall portion being engaged by the peripheral skirt when said suction cup is engaged with said supporting surface.

BRIEF DESCRIPTION OF THE DRAWINGS

Preferred forms of the present invention will now be described by way of example with reference to the accompanying drawings wherein.

DETAILED DESCRIPTION OF THE PREFERRED EMBODIMENTS

In the following description, the preferred embodiments of the present invention are described as containers to receive air fresheners or to dispense products such as dental floss. However, it should be appreciated that containers according to the present invention could be adapted to contain or dispense a wide variety of products such as disinfectants, deodorisers, adhesive tape, twine and other similar products.

In FIGS. 1 to 6 of the accompanying drawings, there is schematically depicted a container 10 which in this embodiment receives a cylindrical block of air freshener material 11. More particularly the block 11 is of annular shape so as to have a longitudinally extending cylindrical central wall 12.

The container 10 has a hollow body 13, including an end (transverse) wall 14, provided with a variety of apertures 15 so that a vapour to be dispensed from the block 11 may pass to the surrounding atmosphere.

Depending from the wall 14 is a peripheral skirt 16 generally surrounding the wall 14. The skirt 16 includes a first skirt flange 17 spaced radially from a second skirt flange 18. In this respect, it should be appreciated that the container 10 has a longitudinal central axis 19. As the container 10 is of a generally circular configuration the flanges 17 and 18 are generally cylindrical and have located between them an annular space 20.

Also depending from the wall 14 is a hollow stem 21 which is of a cylindrical configuration so as to generally enclose a central passage 22.

The skirt flange 17 terminates with a circular extremity 23 while the skirt flange 18 terminates with a circular extremity 24.

Secured to the hollow body 13 is a suction cup 25 having a central projection 26 received within the passage 22. The stem 21 has inwardly extending projections or barbs 27 which engage the projection 26 to captively locate the projection 26 within the passage 22. As the projections 26 form passages in the stem 21, the hollow body 13 cannot rotate relative to the cup 25.

The cup 25 has an annular flange 28 which tapers in thickness from the projection 26 to a peripheral wall 29. The wall 29 has a first wall portion 30 from which there extend wall portions 31 and 32. The wall portions 31 and 32 are separated by an annular groove 33. The wall portion 30 is annular and is received within the annular space 20.

The wall portion 32 diverges from the wall portion 31 so as to have an annular extremity 34 aligned with the extremity 24 of the hollow body 13.

Figure 1:
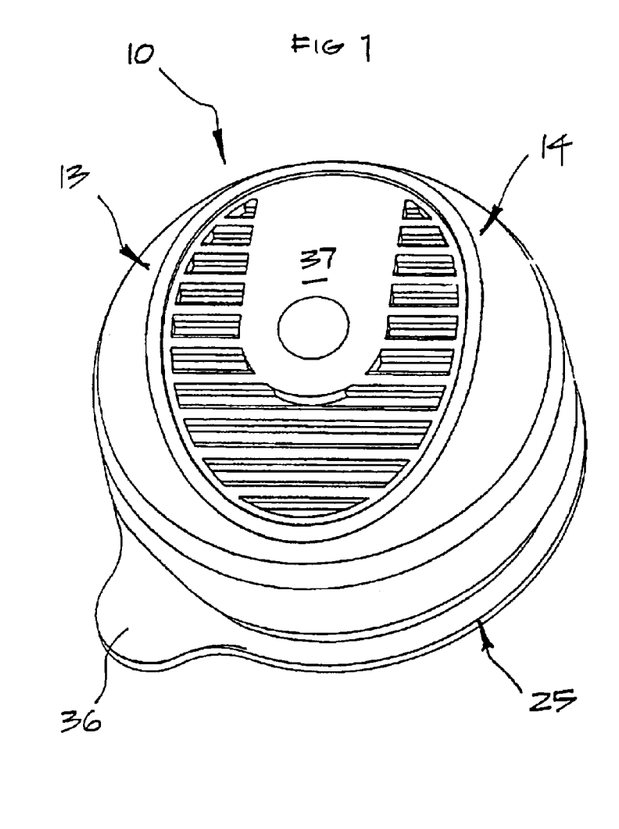
FIG. 1 is a schematic top perspective view of a container to receive a substance to act as an air freshener.
Figure 2:
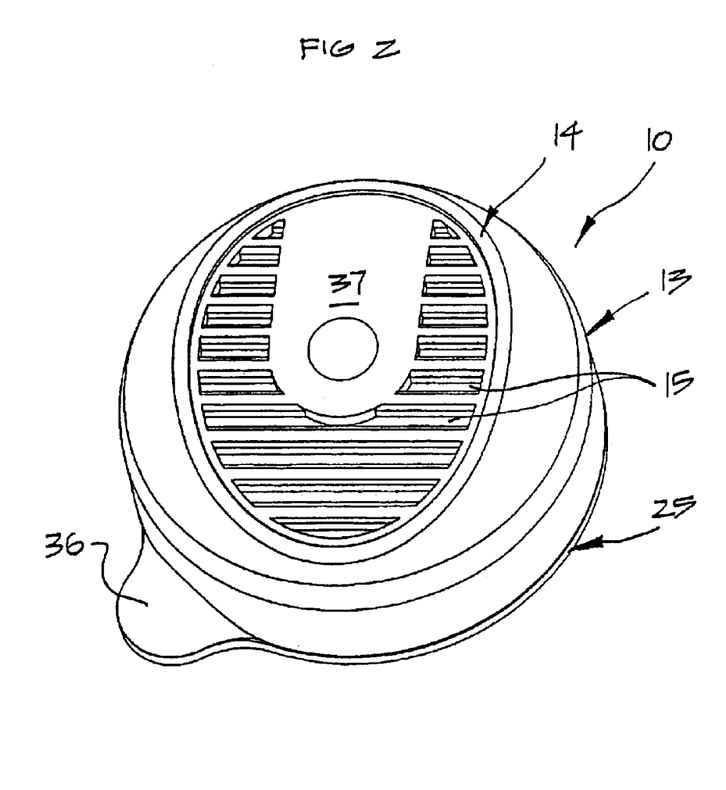
FIG. 2 is a schematic top perspective view of the container of FIG. 1.
Figure 3:
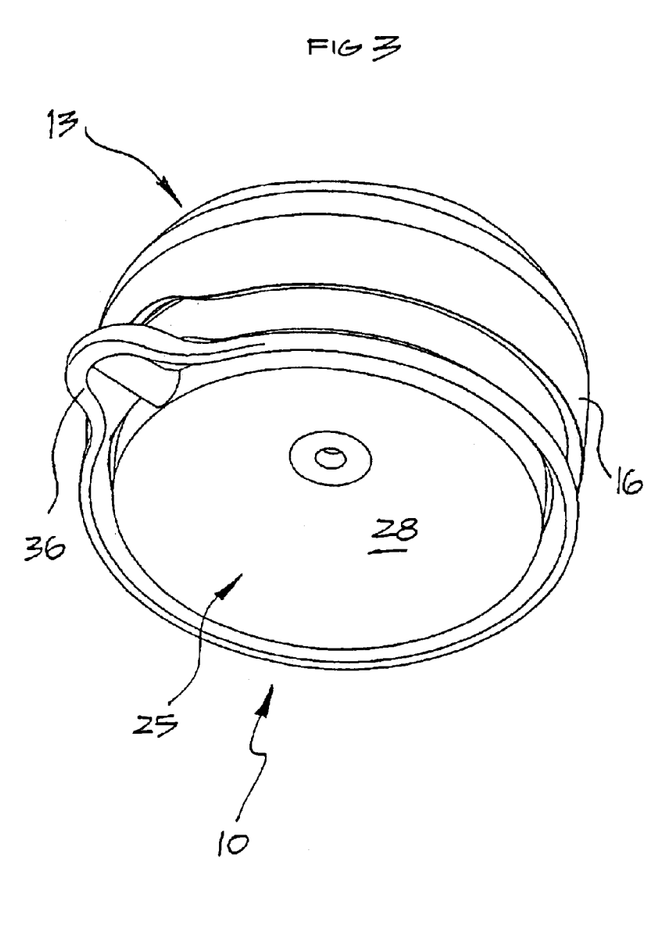
FIG. 3 is a schematic bottom perspective view of the container as illustrated in FIG. 1.
Figure 4:
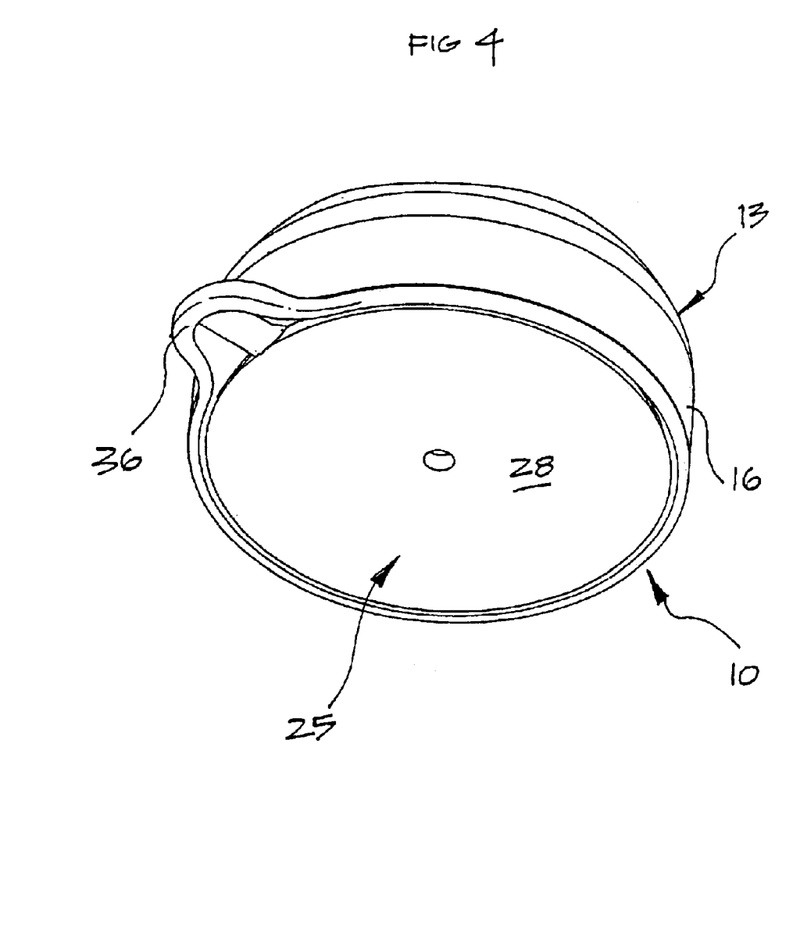
FIG. 4 is a schematic bottom perspective view of the container as illustrated in FIG. 2.
Figure 5:
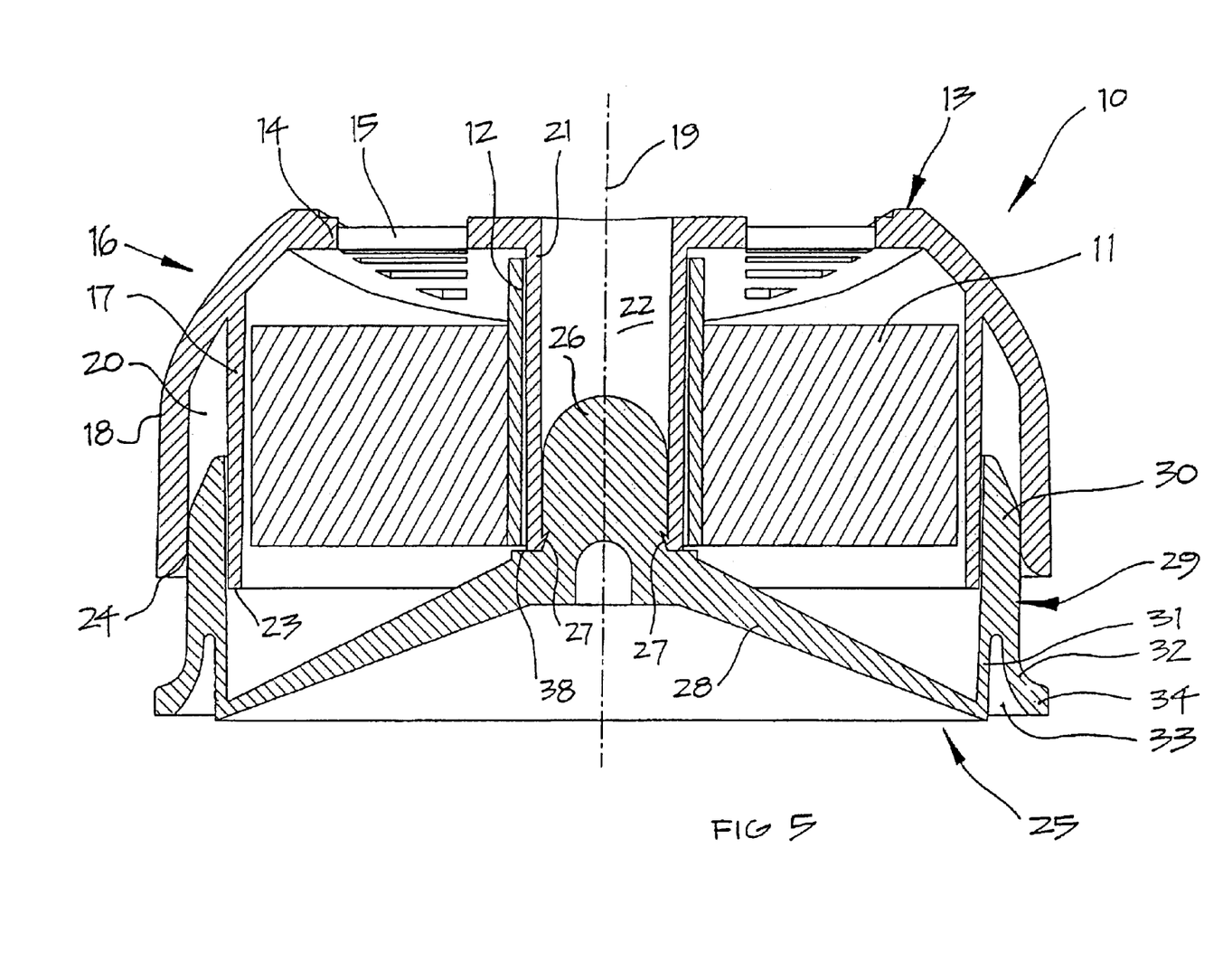
FIG. 5 is a schematic section side elevation of the container of FIGS. 1 to 3.
Figure 6:
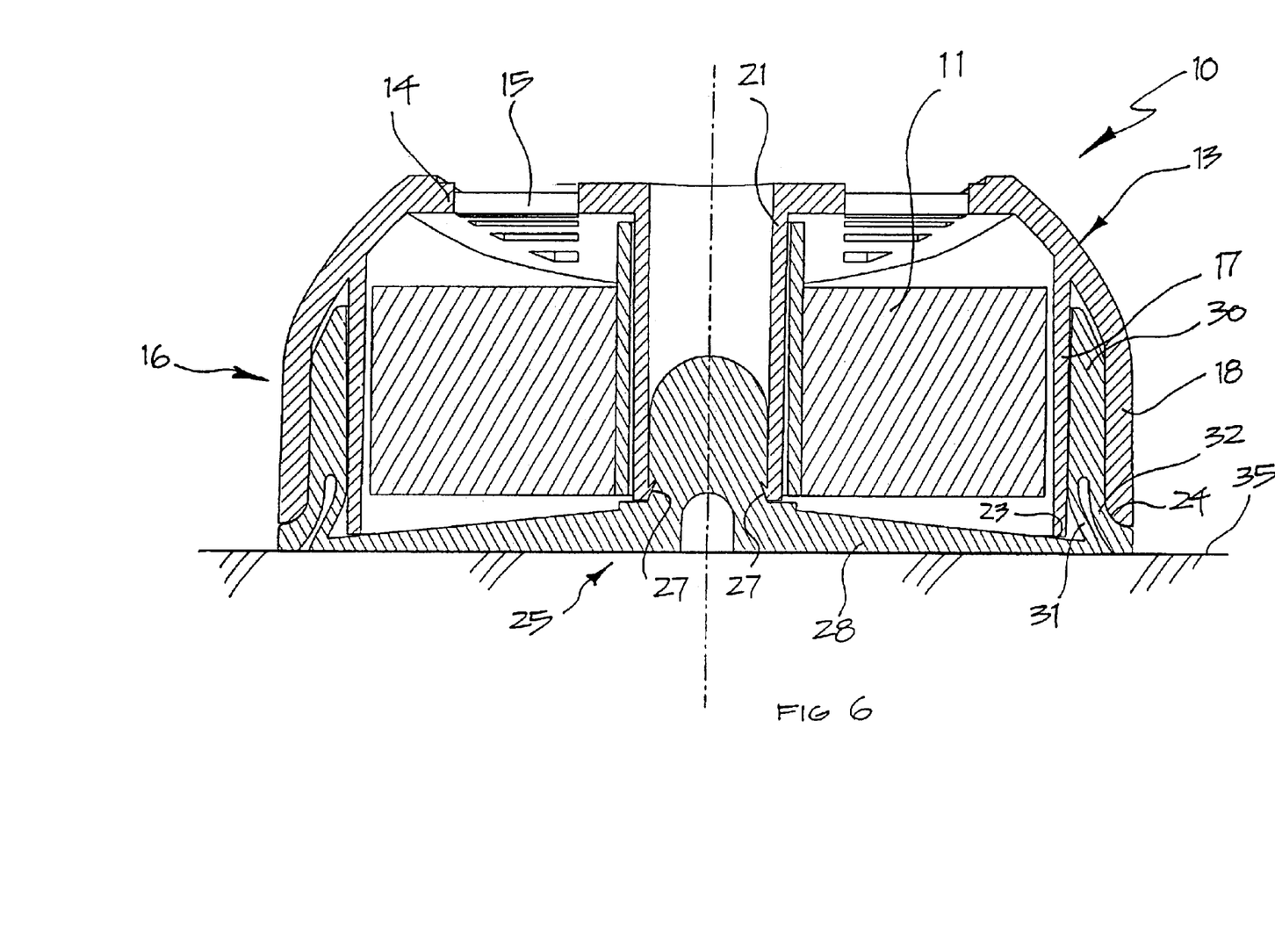
FIG. 6 is a further schematic section side elevation of the container of FIGS. 2 to 4.
Figure 7:
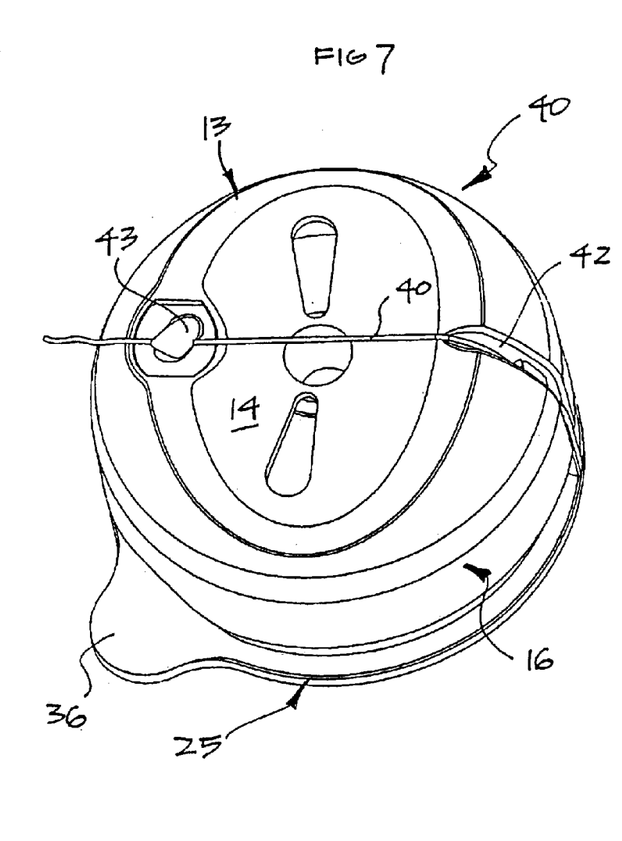
FIG. 7 is a schematic top plan view of a container to dispense dental floss.
Figure 8:
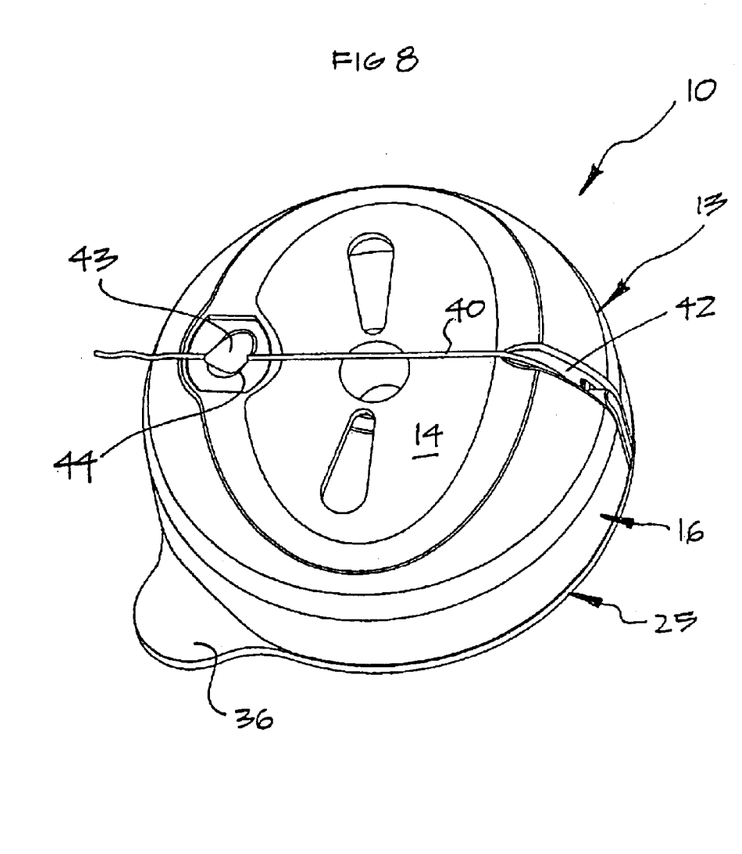
FIG. 8 is a schematic top perspective view of a container of FIG. 7.
Figure 9:
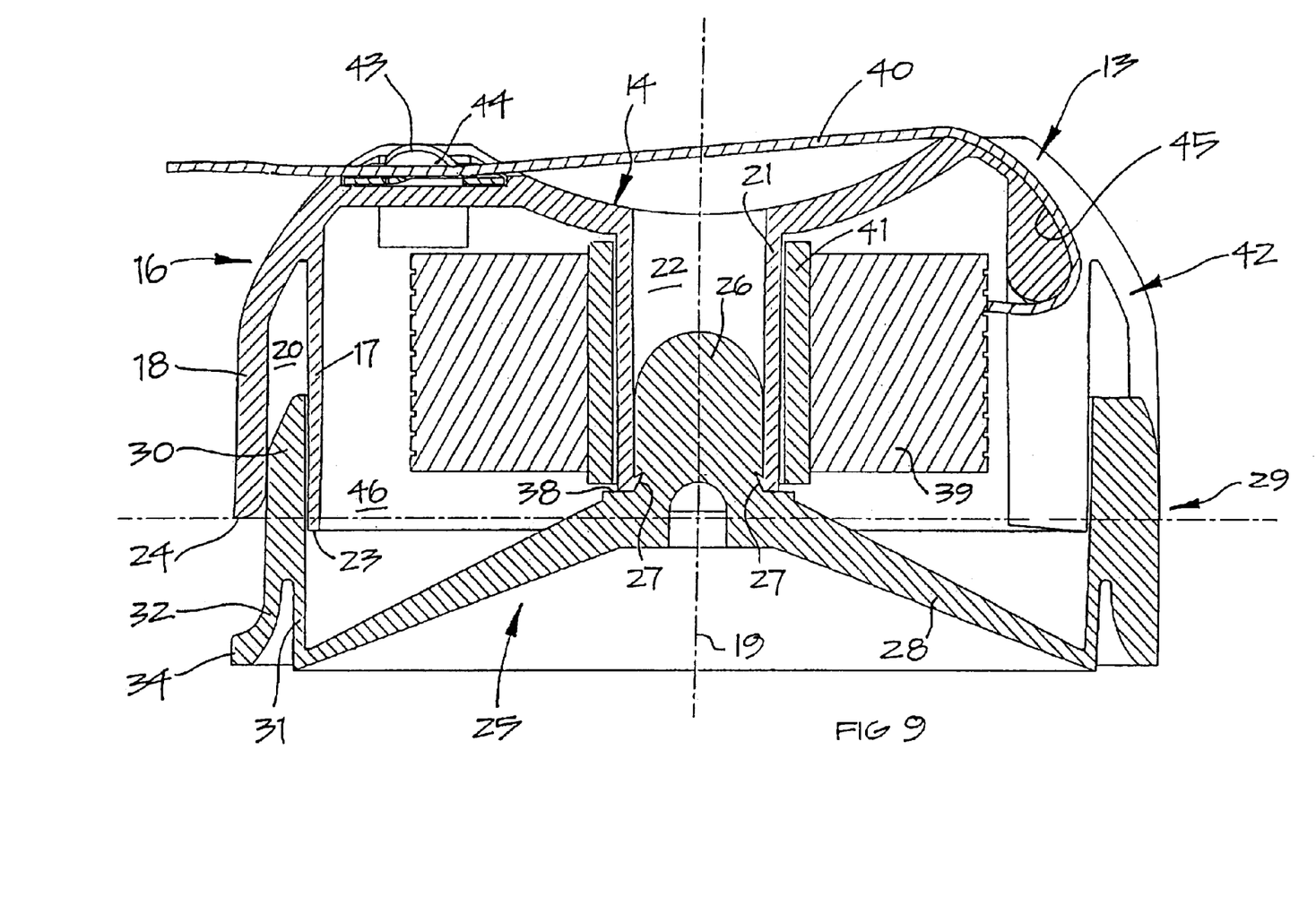
FIG. 9 is a schematic section side elevation of the container as illustrated in FIG. 7.
Figure 10:
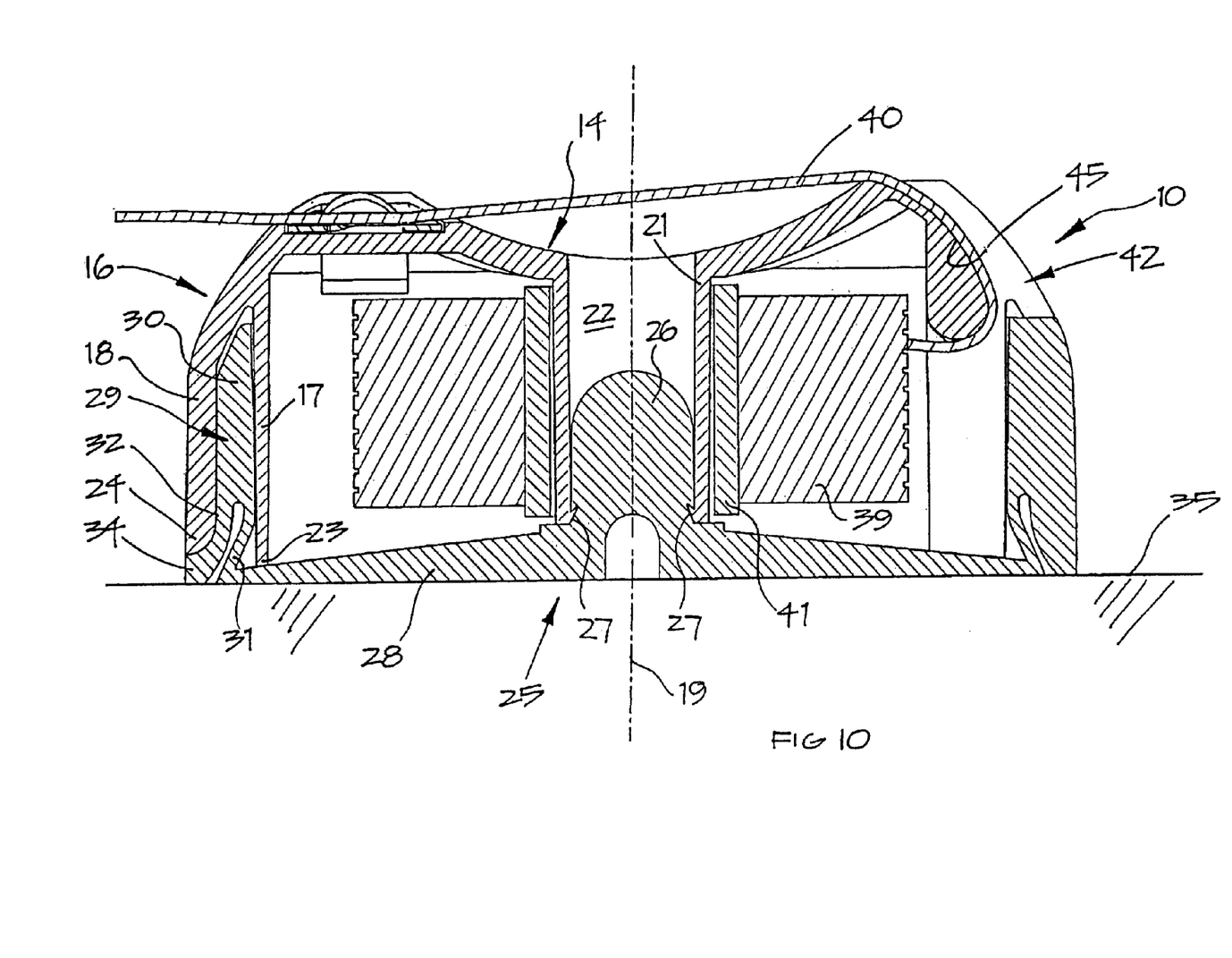
FIG. 10 is a schematic section side elevation of the container as illustrated in FIG. 8.

The hollow body 13 is preferably a moulding of resilient plastics material. The suction cup 25 is resilient elastomeric material which is resiliently deformed by a user pressing on the body 13 toward a supporting surface 35 (which may be a bathroom tile). In FIG. 5, the container 10 is illustrated in a relaxed configuration while in FIG. 6 it is illustrated as applied to the surface 35 with the cup 25 securing the container 10 to the surface 35. As best seen in FIG. 6, the cup 25 is resiliently deformed against the surface 35, with the wall portion 30 substantially filling the space 20 and the wall portions 31 and 32 further resiliently deformed so that the extremity 24 is abutting or is located adjacent the extremity 34. In this configuration it is difficult for a user to dislodge the container 10 by manipulation of the body 13. By having the extremity 24 engaged with or located adjacent the extremity 34, the body 13 is substantially prevented from tilting with respect to the longitudinal axis 13 and therefore the surface 35 and cup 25. It should also be noted that the lower wall portion 31 deflects radially outwardly to permit the flange 28 to deform and engage the surface 35.

In a further embodiment, the skirt flange 18 would abut or be located adjacent the surface 35 rather than the extremity 34 to inhibit tilting of the body 13.

To facilitate removal of the container 10 from the supporting surface 35 there is extending from the wall portion 32 a tab 36 which is gripped by the user and manipulated to deform the radial extremities of the flange 28 and therefore break contact between the cup 25 and the surface 35.

When applying the container 10 to the surface 35 a user preferably applies a force to the central area 37 so that the force is transmitted to the suction cap 35 by the stem 21. More particularly the stem 21 engages an annular surface 38 of the cup 25.

To facilitate deformation of the flange 28, it is connected to the lower wall portion 31 by a thin wall section. As mentioned previously the flange 28 tapers in thickness from the projection 26 towards the wall 29.

It can be further noted from FIG. 6 that the flange 17, and more particularly its extremity 23, also engages the flange 28. Contact of the extremity 23 with the flange 28 facilitates contact between the cup 25 and the supporting surface 35.

In FIGS. 7 to 10 of the accompanying drawings, there is schematically depicted a modification of the container 10 of FIGS. 1 to 6. In this embodiment the same reference numerals have been employed.

In the embodiment of FIGS. 7 to 10 the container 10 receives a reel 39 of dental floss 40. The reel 39 includes an annular inner wall 41 which is slidably received on the stem 21 to the mid-rotation of the reel 39 about the longitudinal axis 19. The end wall 14 is provided with a slot 42 through which the dental floss 40 passes to a cutting blade 43. The cutting blade 43 is of a conventional arrangement in that it provides a tapered slot 44 in to which the floss 40 passes to be severed.

The wall portion 30 together with the wall portion 31 are repositioned to fill portion of the slot 42.

In the embodiment of FIGS. 7 to 10, normal forces applied to the dental floss 40 are not transmitted to the cup 35 in a manner which would remove the cup 25 from the surface 35.

In addition to the slot 42 the body 13 is provided with a smooth arcuate surface 45 over which the dental floss 40 is drawn to pull it from within the container 10.

With particular reference to the embodiment of FIGS. 7 to 10, the hollow body 13 and cup 25 co-operate to provide a generally closed space 46 which receives the reel 39.

Still further with reference to the embodiment of FIGS. 7 to 10, the container 10 is adapted to be located against a tiled surface and therefore can be located in areas for convenient use and which make the container 10 visually apparent to remind people to use dental floss.

What is claimed is:

1. A container to receive a product, said container having: a hollowed body within which the product is to be supported, said body having a peripheral skirt generally surrounding a transverse wall, said peripheral skirt having an extremity and a recess extending from the extremity inwardly of the peripheral skirt, and a suction cup having a central portion attached to the transverse wall, and a cup flange extending from the central portion generally towards the peripheral skirt but spaced therefrom, said suction cup further having a suction cup wall extending ram the cup flange and into said recess; said suction cup is secured to a supporting surface by applying a force to the hollowed body towards said suction cup to resiliently deform the suction cup against said supporting surface and to further cause movement of the suction cup wall into said recess; and wherein said container is of a generally circular configuration so that said recess is annular and said suction cup wall is annular.

2. The container of claim 1 wherein said transverse wall is an end wall and said product is to be located between said transverse wall and cup flange.

3. The container of claim 1 wherein said hollowed body is relatively stiff relative to said suction cup.

4. The container of claim 1 wherein said recess is a space between a first skirt flange and a second skirt flange of said peripheral skirt.

5. The container of claim 1 wherein said suction cup is provided with a tab projecting outwardly of said peripheral skirt which is gripped to deform the suction cup to release the suction cup from said supporting surface.

6. The container of claim 1 wherein there is extending from said transverse wall, a hollow stem to which said suction cup is attached by a suction cup projection extending into said stem.

7. The container of claim 1 wherein said peripheral skirt and said cup flange each have one of a projection or opening wherein said projection will enter said opening to prevent relative rotation of said hollow body and said suction cup.

8. The container of claim 1 further including dental floss disposed within said hollow body.

9. A container to receive a product, said container having: a hollow body within which the product is to be supported, said body having at least one peripheral skirt generally surrounding a transverse wall, a suction cup having a central portion attached to the transverse wall, and a cup flange extending from the central portion generally towards the peripheral skirt but spaced therefrom, and wherein said suction cup is secured to a supporting surface by applying a force to said transverse wall towards said suction cup to resiliently deform the suction cup against said supporting surface, so that said peripheral skirt is moved to a position terminating adjacent or is abutting said cup flange or supporting surface when said suction cup is secured to said supporting surface to inhibit tilting of said hollow body relative to said suction cup and a disengagement of said suction cup from said supporting surface, wherein said peripheral skirt has a recess facing said cup flange, and said cup flange has a cup wall moveably received within said recess.

10. The container of claim 9 wherein the container is of a generally circular configuration so that said recess is annular and said suction cup wall is annular.

11. The container of claim 9 wherein said recess is a space between a first skirt flange and a second skirt flange of said peripheral skirt.

12. The container of claim 9 wherein said transverse wall is an end wall and said product is to be located between said transverse wall and cup flange.

13. The container of claim 9 wherein said hollow body is relatively stiff relative to said suction cup.

14. The container of claim 9 wherein said suction cup is provided with a tab projecting outwardly of said skirt which is gripped to deform the suction cup to release the suction cup from said supporting surface.

15. The container of claim 9 wherein there is extending from said transverse wall a hollow stem to which said suction cup is attached by a suction cup projection extending into said stem.

16. The container of claim 9 wherein said suction cup wall includes spaced wall portions adjacent said cup flange, the spaced wall portions being spaced by a recess surrounding said cup flange.

17. The container of claim 9 wherein said wall portions include an inner and an outer wall portion, with said outer wall portion being engaged by the peripheral skirt when said suction cup is engaged with said supporting surface.

18. The container of claim 9 wherein said peripheral skirt and said cup flange each have one of a projection on opening wherein said projection will enter said opening to prevent relative rotation of said hollow body and said suction cup.

19. A container to receive dental floss, said container having:
   a hollowed body within which the dental floss is to be supported, said body having a peripheral skirt generally surrounding a transverse wall, said peripheral skirt having an extremity and a recess extending from the extremity inwardly of the peripheral skirt, said body having a slot through which said dental floss can pass from said hollow; and
   a suction cup having a central portion attached to the transverse wall, and a cup flange extending from the central portion generally towards the peripheral skirt but spaced therefrom, said suction cup further having a suction cup wall extending from the cup flange and into said recess; and wherein
   said suction cup is secured to a supporting surface by applying a force to the hollow body towards said suction cup to resiliently deform the suction cup against said supporting surface and to farther cause movement of the suction cup wall into said recess.

* * * * *